United States Patent
Lura et al.

(10) Patent No.: US 11,103,626 B2
(45) Date of Patent: Aug. 31, 2021

(54) INFUSATE HOLDER

(71) Applicant: Medtronic, Inc., Minneapolis, MN (US)

(72) Inventors: David B. Lura, Maple Grove, MN (US); Martin T. Gerber, Maple Grove, MN (US); Christopher M. Hobot, Rogers, MN (US); Thomas E. Meyer, Stillwater, MN (US); Jin Huang, Shanghai (CN)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/588,806

(22) Filed: May 8, 2017

(65) Prior Publication Data

US 2017/0239411 A1     Aug. 24, 2017

Related U.S. Application Data

(63) Continuation-in-part of application No. 15/219,238, filed on Jul. 25, 2016, now Pat. No. 10,874,788.

(60) Provisional application No. 62/196,891, filed on Jul. 24, 2015.

(51) Int. Cl.
| | |
|---|---|
| *A61M 1/16* | (2006.01) |
| *A61M 1/26* | (2006.01) |
| *A61K 33/00* | (2006.01) |
| *A61K 33/14* | (2006.01) |
| *A61M 1/34* | (2006.01) |

(52) U.S. Cl.
CPC .......... *A61M 1/1668* (2014.02); *A61K 33/00* (2013.01); *A61K 33/14* (2013.01); *A61M 1/1656* (2013.01); *A61M 1/1666* (2014.02); *A61M 1/1672* (2014.02); *A61M 1/267* (2014.02); *A61M 1/3462* (2013.01); *A61M 2205/6036* (2013.01); *A61M 2209/08* (2013.01); *A61M 2209/082* (2013.01)

(58) Field of Classification Search
None
See application file for complete search history.

(56) References Cited

U.S. PATENT DOCUMENTS

| | | |
|---|---|---|
| 474,782 A | 5/1892 | Stokoe |
| 503,226 A | 8/1893 | Anderson |
| 564,320 A | 7/1896 | Underwood |
| 1,683,723 A | 9/1928 | William |

(Continued)

FOREIGN PATENT DOCUMENTS

| | | |
|---|---|---|
| CN | 202105667 | 1/2012 |
| EP | 2735322 | 5/2014 |

(Continued)

OTHER PUBLICATIONS

[NPL637] International Search Report, Application PCT/US2016/043935, dated Feb. 2, 2017. (Year: 2017).*

(Continued)

*Primary Examiner* — Jonathan M Peo

(57) ABSTRACT

The invention relates to an infusate holder for use in dialysis. The infusate holder can include one or more interior compartments for holding infusate containers or infusates. The interior compartments are aligned to cooperate with fluid connectors of a dialysis system, ensuring that the proper infusates are added to the dialysis system at a proper location.

22 Claims, 10 Drawing Sheets

(56) References Cited

U.S. PATENT DOCUMENTS

| | | | |
|---|---|---|---|
| 4,747,822 A * | 5/1988 | Peabody | A61M 1/28 604/29 |
| 4,784,495 A * | 11/1988 | Jonsson | A61M 1/1656 137/88 |
| 5,032,265 A * | 7/1991 | Jha | A61M 1/1668 210/195.2 |
| 5,141,493 A | 8/1992 | Jacobsen | |
| 5,643,201 A * | 7/1997 | Peabody | A61M 1/1686 604/31 |
| 6,355,161 B1 | 3/2002 | Shah | |
| 2002/0023879 A1* | 2/2002 | Hadden | A61M 1/16 210/646 |
| 2002/0091371 A1 | 7/2002 | Ritter | |
| 2006/0115395 A1* | 6/2006 | Taylor | A61M 1/1656 422/261 |
| 2010/0051552 A1 | 3/2010 | Rohde | |
| 2010/0312172 A1* | 12/2010 | Hoffman | A61M 1/1696 604/28 |
| 2011/0017665 A1 | 1/2011 | Updyke | |
| 2011/0249916 A1 | 10/2011 | Herrenbauer | |
| 2012/0199205 A1* | 8/2012 | Eyrard | A61M 1/1668 137/1 |
| 2013/0001165 A1 | 1/2013 | Pohlmeier | |
| 2013/0015302 A1 | 1/2013 | Gkhan rter | |
| 2013/0062265 A1 | 3/2013 | Balschat | |
| 2013/0190681 A1* | 7/2013 | Jansson | A61J 1/2093 604/28 |
| 2014/0018727 A1* | 1/2014 | Burbank | A61M 1/281 604/28 |
| 2014/0217029 A1 | 8/2014 | Meyer | |
| 2017/0021079 A1 | 1/2017 | Lura | |

FOREIGN PATENT DOCUMENTS

| | | | | |
|---|---|---|---|---|
| JP | 2006325668 A | | 12/2006 | |
| WO | 9937342 A1 | | 7/1999 | |
| WO | WO 0057935 A1 | * | 10/2000 | A61L 2/0023 |
| WO | WO2000057935 A1 | | 10/2000 | |
| WO | WO2009064984 | | 5/2009 | |
| WO | 20111113572 A1 | | 9/2011 | |
| WO | 20122138604 A2 | | 10/2012 | |
| WO | 2014121158 A1 | | 8/2014 | |
| WO | 2015071247 A1 | | 5/2015 | |
| WO | WO2017/019640 A1 | | 2/2017 | |

OTHER PUBLICATIONS

International Search Report, PCT/US2017/025868, dated Jun. 29, 2017, 5 total pages. (Year: 2017).*
[NPL635] International Search Report, Application PCT/2016/043948, dated Feb. 2, 2017.
[NPL636] Written Opinion, Application PCT/2016/043948, dated Feb. 2, 2017.
[NPL637] International Search Report, Application PCT/US2016/043935, dated Feb. 2, 2017.
[NPL638] Written Opinion, Application PCT/US2016/043935, dated Feb. 2, 2017.
PCT/US2017/025868 Written Opinion dated Jun. 29, 2017.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
[NPL635] International Search Report, Application PCT/US2016/043948, dated Feb. 2, 2017.
[NPL638] Written Opinion, Application PCT/2016/043935, dated Feb. 2, 2017.
International Search Report, Application No. PCT/US2017/031533, dated Aug. 9, 2017.
International Search Report, Application No. PCT/US2017/031520, dated Aug. 7, 2017.
European Office Action for App. No. 17724468.8, dated May 14, 2020.
Chinese Office Action for App. No. 201680041414.6, dated Jun. 9, 2020.
Chinese Office Action for App. No. 201680041324.7, dated Jun. 1, 2020.
Chinese Office Action for App. No. 201680041413.1, dated May 28, 2020.
European Search Report for App. No. 16760215.0, dated May 7, 2020.
European Search Report for App. No. 17724689.9, dated May 14, 2020.
Chinese Office Action for App. No. 201680041414.6, dated Oct. 20, 2020.

* cited by examiner

INFUSATE HOLDER

CROSS-REFERENCE TO RELATED APPLICATIONS

This application is a continuation-in-part of U.S. patent application Ser. No. 15/219,238, filed on Jul. 25, 2016, which claims the benefit of U.S. Provisional Patent Application No. 62/196,891, filed on Jul. 24, 2015, the entire contents of which is incorporated herein by reference.

FIELD OF THE INVENTION

The invention relates to and infusate holder for use in dialysis. The infusate holder can include one or more interior compartments for holding infusate containers or infusates. The interior compartments are aligned to cooperate with fluid connectors of a dialysis system, ensuring that the proper infusates are added to the dialysis system at a proper location.

BACKGROUND

During priming of a dialysis system and during dialysis treatment, specific concentrations of specific solutions, such as sodium chloride, sodium bicarbonate, and cation infusates, must be added to the dialysate flow path. Further, many cations, such as potassium, calcium and magnesium, can cross the dialyzer and be removed from a patient during dialysis. The cations must be added back into the dialysate to maintain the concentration of the cations at a desired level. Sodium bicarbonate can be used during dialysis as a buffer to control the pH of the dialysate and to treat acidosis by delivering bicarbonate across the dialysis membrane to the patient receiving a treatment. The amounts of sodium chloride, sodium bicarbonate and other cations added to dialysate should be closely monitored and controlled. Further, the amounts of each of the solutions necessary can vary considerably.

There is a need for ensuring proper solutes are added in proper amounts to the dialysate. To facilitate use of dialysis by personnel, systems and methods are needed that can ensure that any of the solutes or solutions are properly added to the dialysis system. Further, systems and methods are needed to ensure that all necessary components to be used during dialysis are connected to the dialysis system at the correct locations for a dialysate flow path. There is a further need for a system that reduces the number of containers required to be cleaned and disinfected each time the dialysis system is used.

SUMMARY OF THE INVENTION

The first aspect of the invention relates to an infusate holder. In any embodiment of the first aspect of the invention, the infusate holder can include a base; exterior walls connected to the base and upwardly extending from the base; at least two compartments complementary to at least two different infusates the at least two compartments having an interior wall connected to the base and upwardly extending from the base and defining an interior compartment of the infusate holder wherein a vertical axis of the interior compartment is aligned to a fluid connector disposed on a dialysis machine wherein the infusate holder is complementary to a receiving compartment on a dialysis machine.

In any embodiment, at least one interior compartment can contain a filter and a draw tube extending downwardly through the filter.

In any embodiment, the infusate holder can include a lid covering a top of the infusate holder, the lid having openings aligned with the interior compartments.

In any embodiment, the lid can form an air-tight seal with the interior compartments.

In any embodiment, the at least one exterior wall and at least one interior wall can define at least one interior compartment having an inwardly tapered bottom portion.

Any of the features disclosed as being part of the first aspect of the invention can be included in the first aspect of the invention, either alone or in combination.

The second aspect of the invention is drawn to a dialysis system. In any embodiment, the dialysis system can include an infusate holder; the infusate holder having a base; exterior walls connected to the base and upwardly extending from the base; at least two compartments complementary to at least two different infusates the at least two compartments having an interior wall connected to the base and upwardly extending from the base and defining an interior compartment of the infusate holder wherein a vertical axis of the interior compartment is aligned to a fluid connector disposed on a dialysis machine wherein the infusate holder is complementary to a receiving compartment on a dialysis machine; and the dialysis system also including a dialysis machine having (i) a dialysate flow path; (ii) a receiving compartment for the infusate holder; the receiving compartment having a size and shape complementary to the infusate holder; (iii) two or more fluid connectors fluidly connecting the one or more infusates to the dialysate flow path; and (iv) at least one pump controlling fluid movement through the fluid connectors.

In any embodiment, the interior compartments can be sized and shaped complementary to at least two different infusate containers; the fluid connectors fluidly connectable to each of the infusate containers.

In any embodiment, the infusate containers can be selected from a sodium bicarbonate container, a sodium chloride container, a cation infusate container, and combinations thereof.

In any embodiment, the dialysis system can include a lid for the infusate holder, the lid having two or more openings aligned with the interior compartments.

In any embodiment, the infusate holder can have at least three interior compartments.

In any embodiment, the interior compartments can contain a powder, solid, or a solution of the infusates.

In any embodiment, the infusates can be from the group of sodium bicarbonate, sodium chloride, and cation infusates.

In any embodiment, the lid can form an air tight seal with the infusate holder.

In any embodiment, the dialysis system can include draw tubes in each interior compartment, the draw tubes extending downwardly from the openings in the lid to the interior compartment; the draw tubes fluidly connectable to the fluid connectors.

In any embodiment, the dialysis system can include a filter within at least one interior compartment, the filter disposed above the base of the infusate holder; the draw tube extending through the filter.

In any embodiment, the dialysis system can include a locking mechanism preventing the infusate holder from moving after insertion into the receiving compartment when the locking mechanism is in a locked state.

In any embodiment, the infusate holder can be removable from the dialysis machine.

In any embodiment, the system can include a handle disposed on an exterior wall of the infusate holder.

In any embodiment, at least one pump can be a bidirectional pump.

In any embodiment, the sodium chloride and sodium bicarbonate can be fluidly connectable to a valve; wherein the valve is fluidly connected to the dialysate flow path upstream of a sorbent cartridge and downstream of the sorbent cartridge.

In any embodiment, the dialysis system can include at least one fitting feature on an exterior surface of the infusate holder; the fitting feature complementary to a corresponding fitting feature on an interior surface of the receiving compartment.

Any of the features disclosed as being part of the second aspect of the invention can be included in the second aspect of the invention, either alone or in combination.

DETAILED DESCRIPTION OF THE INVENTION

Figure 1:
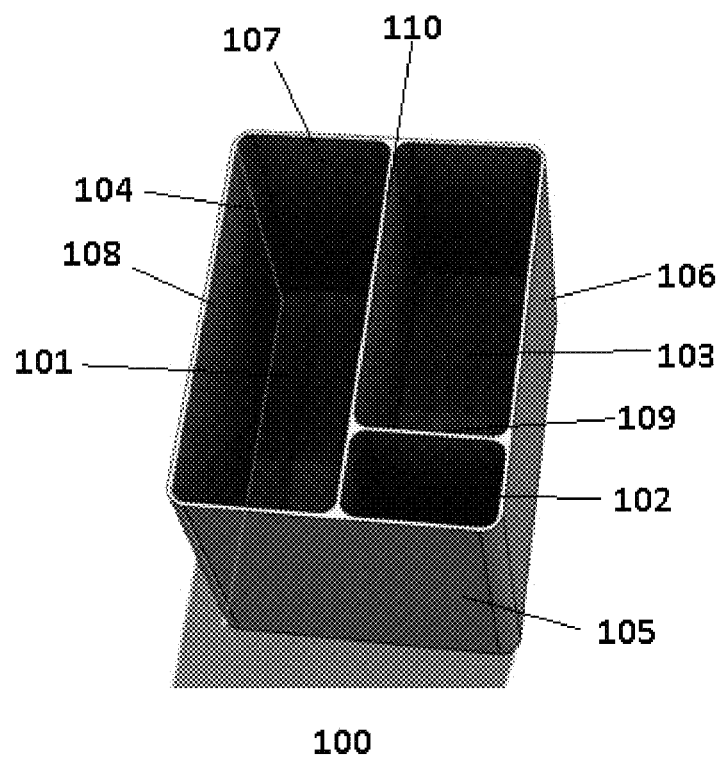
FIG. 1 is an infusate holder having three interior compartments.

Unless defined otherwise, all technical and scientific terms used herein generally have the same meaning as commonly understood by one of ordinary skill in the relevant art.

The articles "a" and "an" are used to refer to one or to over one (i.e., to at least one) of the grammatical object of the article. For example, "an element" means one element or over one element.

The term "air tight seal" refers to two components that, when connected, do not allow air or fluid to pass between the components.

The term "aligned" refers to a configuration of components wherein the components are positioned to a particular arrangement of components. For example, a fluid connection can be aligned to a movable connector to form a fluid connection between the components upon being positioned to a proper alignment.

The term "base" refers to a bottom portion of a component.

The term "bi-directional pump" refers to a device configured to perform work on a fluid to cause the fluid to flow alternatively in either of two opposing directions.

A "cation infusate" refers to cations added to a dialysate during dialysis therapy.

The term "cation infusate container" refers to a source from which cations can be obtained. Examples of cations include, but are not limited to, calcium, magnesium and potassium. The source can be a solution containing cations or dry compositions hydrated by the system. The cation infusate container is not limited to cations and may optionally include other substances to be infused into a dialysate or replacement fluid; non-limiting examples can include glucose, dextrose, acetic acid and citric acid.

The term "complementary," as used to describe fitting features, refers to one or more fitting features on a first component designed to pair or mate with one or more fitting features on a second component. For example, a first component may have a receiving compartment of particular dimensions, and the second component may be the same dimensions, such that the second component can mate within the receiving compartment.

The term "comprising" includes, but is not limited to, whatever follows the word "comprising." Use of the term indicates the listed elements are required or mandatory but that other elements are optional and may be present.

The term "connected to" refers to two components in physical contact with each other.

The term "consisting of" includes and is limited to whatever follows the phrase "consisting of". The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "controlling fluid flow" or to "control fluid flow" refers to the ability to cause a fluid to move through a flow path in a specific direction, rate, or route.

A "dialysate flow path" is a route in which a fluid can travel during dialysis.

"Dialysis" or "dialysis therapy" is a type of filtration and/or or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis machine" is a system comprising a dialyzer, pumps, valves and fluid lines used to carry out a dialysis session.

The term "disposed" refers to a first component's placement on a second component.

The term "downstream" refers to a position of a first component in a flow path relative to a second component wherein fluid will pass by the second component prior to the first component during normal operation. The first component can be said to be "downstream" of the second component, while the second component is "upstream" of the first component.

A "draw tube" is a fluid connector extending into an interior space of a component. The passageway can permit a flow of fluid, gas, mixtures of fluid and gas, a slurry, or any material having sufficient flowability properties to permit travel of the material along the pathway.

"Extending downwardly" or to "extend downwardly" refers to a component positioned from a higher elevation to a lower elevation.

An "exterior surface" is the exterior boundary of a component.

An "exterior wall" is a portion of a component separating the interior of the component from the outside environment.

A "filter" is a component that inhibits the passage particulate matter conveyed by a fluid or solution while allowing the passage of the fluid or solution.

A "fitting feature" is any protrusion, indentation, groove, ridge, having any shape, size, or geometry that serves to ensure that only a corresponding fitting feature complementary to the fitting feature is capable of forming a connection or fit to the corresponding fitting feature. The fitting feature also includes non-mechanical means for ensuring complementary connection such as magnets placed at particular locations, or visual or aural indicators such as color, lettering, or sound. The fitting feature can be affixed, integral, or labeled on a component or surface to ensure that a corresponding feature on a desired component or surface can mate or connect to the component or surface having the fitting feature.

A "fluid" is a liquid substance optionally having a combination of gas and liquid phases in the fluid. Notably, a liquid can therefore also have a mixture of gas and liquid phases of matter.

The term "fluid connector," "fluidly connectable," or "fluidly connected" refers to the ability to pass fluid, gas, or mixtures thereof from one point to another point. The two points can be within or between any one or more of compartments, modules, systems, and components.

A "handle" is a component on an infusate holder that can be used to hold the infusate holder while moving the infusate holder.

An "infusate" is any chemical or solution added to a dialysate flow path for priming, cleaning, or performing treatment with a dialysis system.

An "infusate container" is a container adapted to contain one or more fluids for dialysis. The infusate container can at times hold dry chemicals that are later able to be reconstituted with a fluid to form a slurry, mixture, solution, fluid, or material of having sufficient flowability properties to permit travel of the material along a pathway.

An "infusate holder" is a component detachably removable from a dialysis system and configured to hold one or more containers or to hold a solid, powder or solution source of infusates.

An "interior compartment" is a section inside of a component separated from the rest of the component.

The term "interior surface" refers to an interior boundary of a component.

An "interior wall" is a portion inside a component separating the inside of the component into separate compartments.

The term "inwardly tapered" refers to a three-dimensional shape of a component that extends towards a point when moving from the outside of the component to the inside of the component.

A "lid" is a covering for a component.

A "locked state" refers to a configuration of attached components wherein the components cannot easily be detached from one another.

A "locking mechanism" is any mechanism by which one component can be connected to a second component and resist inadvertent disconnection.

An "opening" is a portion of a component having a defined void space. As used in the invention, an opening in a lid refers to a void space through which containers or connectors can be placed.

The term "powder" refers to a substance containing fine, loose particles.

The term "pump" refers to any device that causes the movement of fluids or gases by applying suction or pressure.

A "receiving compartment" is a portion of a container, caddy, device, or system adapted for receiving a component or container.

The term "removable" or "removed" relates to any component of the present invention that can be separated from a system, module, cartridge or any component of the invention.

"Shape" refers to the three dimensional form of a component.

"Size" refers to the area, surface area, or volume of a container or component.

The terms "sodium bicarbonate container" refers to an object that can be a stand-alone enclosure or alternatively can be integrally formed with an apparatus for hemodialysis, hemodiafiltration, or hemofiltration. The object can store a source of sodium bicarbonate in solid and/or solution form, and can be configured to interface with at least one other functional module found in systems for hemodialysis, hemodiafiltration, or hemofiltration. The sodium bicarbonate reservoir or container can contain at least one fluid pathway and include components such as conduits, valves, filters or fluid connection ports.

The terms "sodium chloride container" refers to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. The sodium chloride reservoir or container can contain at least one fluid pathway and include components such as conduits, valves, filters or fluid connection ports.

The term "solid" refers to a state of matter having fixed dimensions.

A "solution" refers to a homogeneous mixture of a solute in a solvent.

The term "sorbent cartridge" refers to a cartridge containing one or more sorbent materials for removing specific solutes from solution. The term "sorbent cartridge" does not require the contents in the cartridge be sorbent based, and the contents of the sorbent cartridge can be any contents that can remove solutes from a dialysate. The sorbent cartridge may include any suitable amount of one or more sorbent materials. In certain instances, the term "sorbent cartridge" refers to a cartridge which includes one or more sorbent materials besides one or more other materials capable of removing solutes from dialysate. "Sorbent cartridge" can include configurations where at least some materials in the cartridge do not act by mechanisms of adsorption or absorption.

The term "upstream" refers to a position of a first component in a flow path relative to a second component wherein fluid will pass by the first component prior to the second component during normal operation. The first component can be said to be "upstream" of the second component, while the second component is "downstream" of the first component.

The term "upwardly extending" makes reference to a feature, such as a wall or a side of geometric shape, that can be used to form a volume from a geometric base. For example, a rectangular base having four sides can extend upwardly to form a cubic volume.

A "valve" is a device capable of directing the flow of fluid or gas by opening, closing or obstructing one or more pathways to allow the fluid or gas to travel in a path. One or more valves configured to accomplish a desired flow can be configured into a "valve assembly."

The term "vertical axis" refers to an imaginary line extending upwardly and downwardly through a point.

Infusate Holder

FIG. 1 illustrates a non-limiting embodiment of an infusate holder 100. The infusate holder 100 includes a base 101 and upwardly extending exterior walls 105, 106, 107, and 108, connected to the base 101 defining an interior space for holding one or more infusates. The infusate holder 100 can include one or more interior walls 109 and 110 connected to the base 101 defining interior compartments 102, 103, and 104 within the infusate holder 100. As illustrated in FIG. 1, the infusate holder 100 can include two interior walls 109 and 110 defining three interior compartments 102, 103, and 104. However, a range of interior walls and interior compartments can be included in the infusate holder 100. For example, the infusate holder 100 can include 2, 3, 4, 5, 6 or more interior compartments. One of skill in the art will understand that several arrangements of interior walls can be included to separate the infusate holder 100 into a range of interior compartments.

Interior compartment 102 can hold a sodium chloride infusate, interior compartment 103 can hold a sodium bicarbonate infusate, and interior compartment 104 can hold a cation infusate. Instead of a single interior compartment 104 for holding a cation infusate, separate cation infusate compartments containing separate cations can be included. A first cation infusate interior compartment can hold a potassium source, while a second cation infusate interior compartment can hold a calcium chloride source, and a third cation infusate interior compartment can hold a magnesium chloride source. Various combinations of cation infusates can be included in the infusate holder 100 in one or more interior compartments.

For use in a dialysis system, the infusate holder 100 can fit within a receiving compartment of a dialysis machine (not shown in FIG. 1). The infusate holder 100 can have a size and shape complementary to the receiving compartment to ensure the infusate holder 100 is properly situated in the receiving compartment. Although the base 101 and upwardly extending exterior walls 105, 106, 107, and 108 in FIG. 1 are arranged in a substantially rectangular shape, numerous sizes and shapes of infusate holder can be used, including square, triangular, ovoid, or circular. The receiving compartment of the dialysis machine can have a corresponding shape to receive the infusate holder 100.

The interior compartments 102, 103, and 104 can hold a solid infusates, infusate solutions, infusate containers containing a solid infusate or infusate solution, or a combination thereof. The interior walls 109 and 110 can be impermeable to fluid, preventing fluid from one interior compartment from entering a different interior compartment. The infusate containers can have a size and shape complementary to the interior compartments. The shaped compartment can be complementary to the solid infusates, infusate solutions, or infusate containers containing a solid infusate or infusate solution to resist pressure change and deformation of the containers and to ensure a sung fit. The interior compartment 102 can have a smaller area than interior compartment 103. The sodium bicarbonate container and/or cation infusate container can have an area too large to fit within interior compartment 102. The user cannot place the sodium bicarbonate container or cation infusate container in interior compartment 102 and the sodium chloride container can have the only size or shape capable of fitting within interior compartment 102. Because the size and shape of the interior compartments are complementary to only one infusate container, the user can only place the infusate containers in the correct interior compartments. Fluid connectors on a dialysis machine (not shown in FIG. 1) can connect to a container in a single interior compartment, ensuring that the correct infusate is connected to the dialysate flow path at the correct location. The fluid connectors can be aligned with a vertical axis of the interior compartments to ensure that the proper fluid connectors are fluidly connected to the proper interior compartments.

Figure 2:
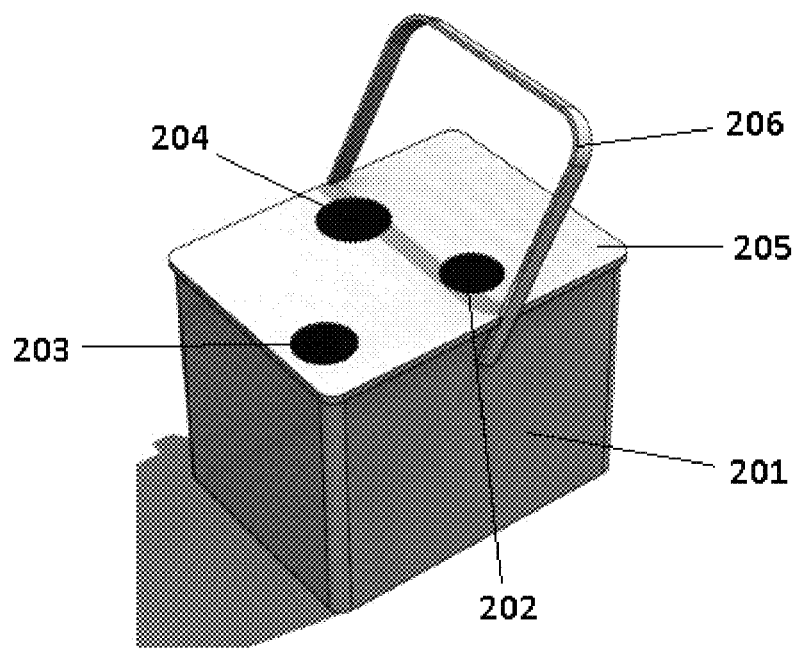
FIG. 2 is an infusate holder including a lid.

FIG. 2 illustrates an infusate holder 201 with a lid 205. The lid 205 can have openings 202, 203, and 204 for connection to a dialysate flow path. The openings 202, 203, and 204 can be aligned with separate interior compartments as illustrated in FIG. 1. Infusate containers, solid infusates, or infusate solutions can be placed in the interior compartments, and fluid connectors from a dialysis machine can be configured to add or remove fluid from the containers or interior compartments. When a solid or powdered infusate source is used, water can be added to the interior compartments or infusate containers to dissolve the solid or powdered infusate, creating an infusate solution of known concentration. The infusate solution can be pumped from the infusate containers or interior compartments into the dialysate flow path. A handle 206 can optionally be included for moving or holding the infusate holder 201.

Infusate containers can be placed in the interior compartments, with the containers extending through the openings 202, 203, and 204 in the lid 205. The infusate containers can include fluid connectors for connection to a dialysis system. Alternatively, fluid connectors on a dialysis machine can extend downwardly through the openings 202, 203, and 204 in the lid 205 to reach an infusate solution in the interior compartments when infusate containers are not used.

Figure 3A:
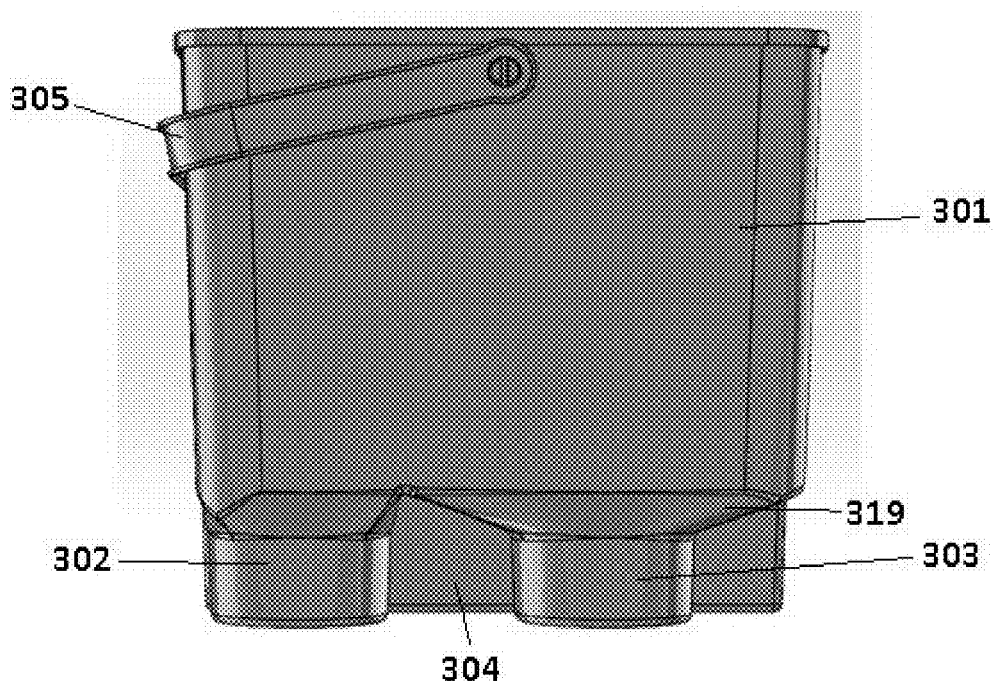
FIGS. 3A-E are an infusate holder for holding a solid, powder, or solution source of the infusates.
Figure 3B:
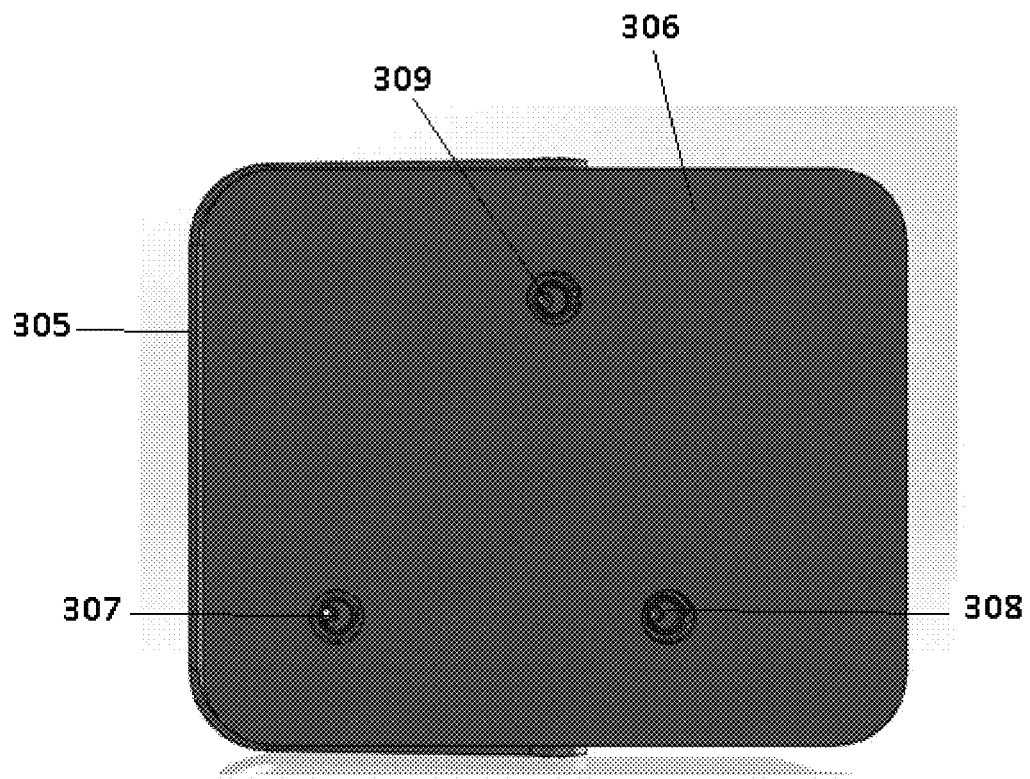
Figure 3C:
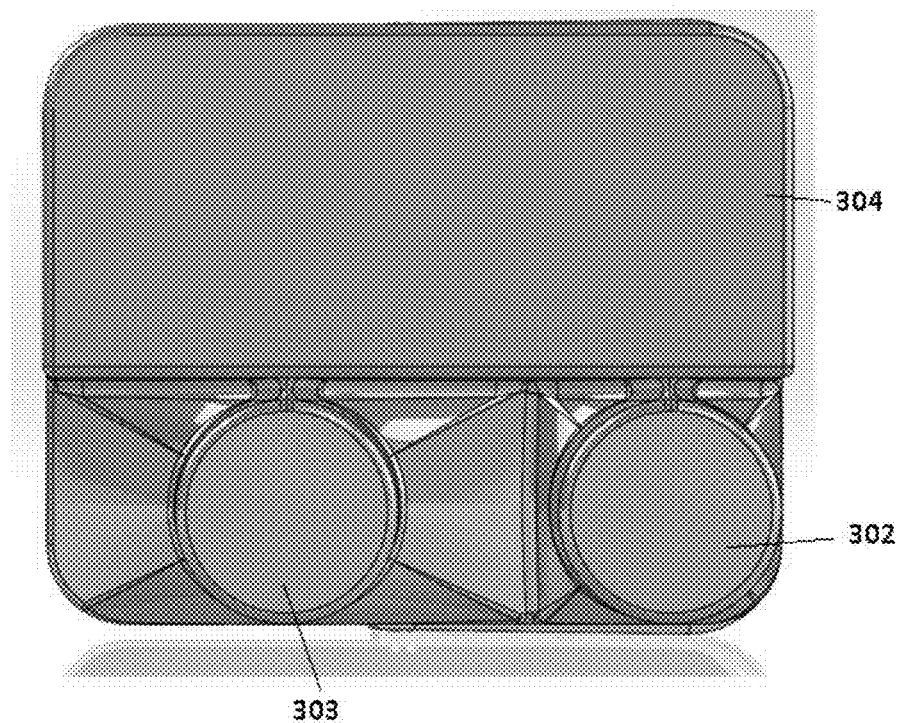
Figure 3D:
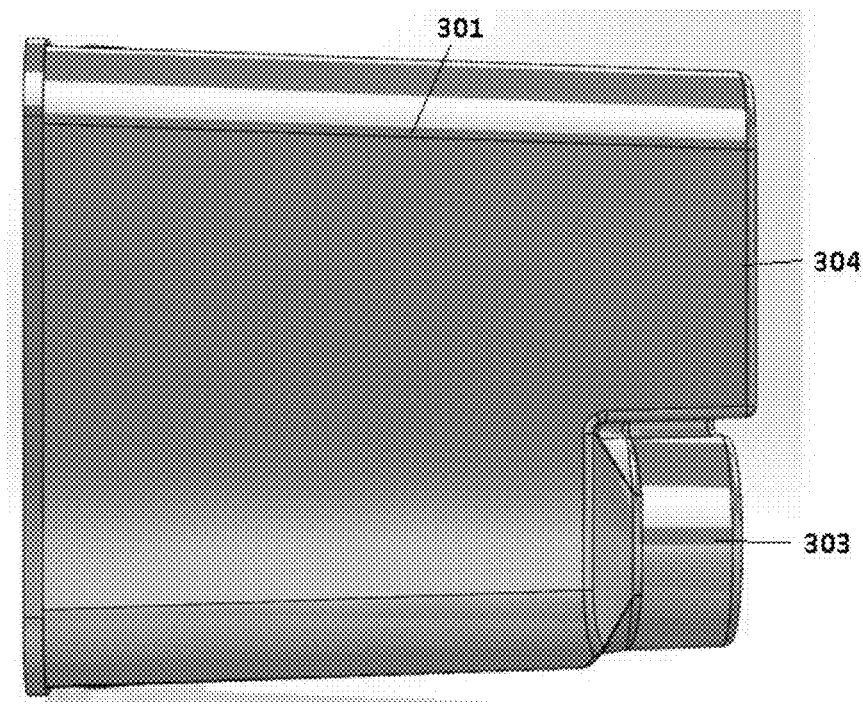
Figure 3E:
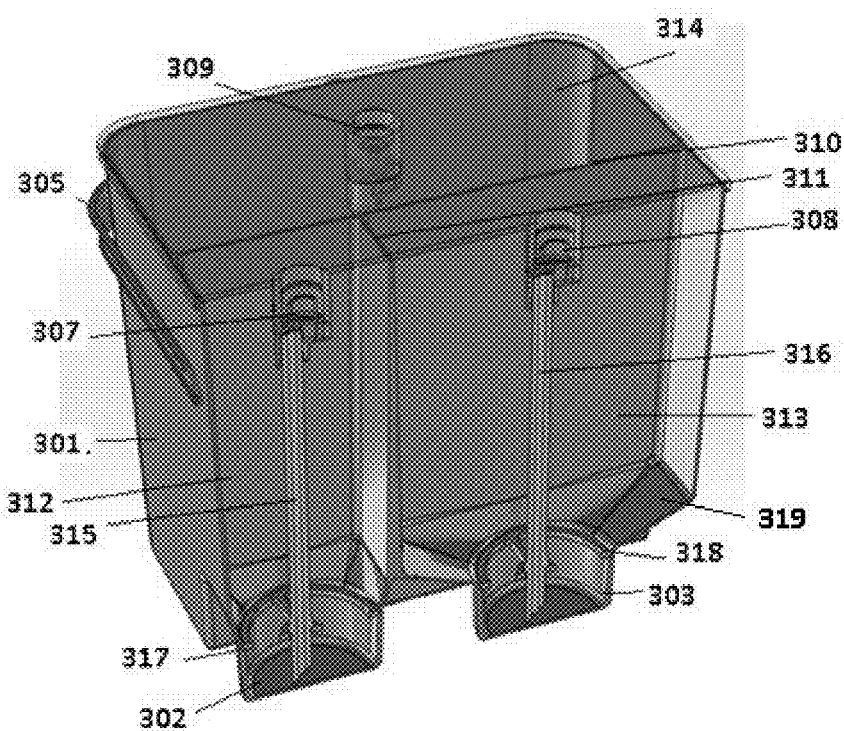

FIGS. 3A-E illustrate an alternative embodiment of an infusate holder. FIG. 3A is a front view of the infusate holder 301, FIG. 3B is a top view of the infusate holder 301, FIG. 3C is a bottom view of the infusate holder 301, FIG. 3D is a side view of the infusate holder 301, and FIG. 3E is a cross-sectional view of the infusate holder 301. The base of the infusate holder illustrated in FIGS. 3A-E has bottom portions 302, 303, and 304 extending downwardly and corresponding to interior compartments, as opposed to the planar base illustrated in FIGS. 1-2. The bottom portions 302, 303, and 304 can hold the infusate solution or the base of one or more infusate containers. For example, bottom portion 302 can hold a sodium chloride solution or the base of a sodium chloride container, bottom portion 303 can hold a sodium bicarbonate solution or a base of a sodium bicarbonate container, and portion 304 can hold a cation infusate solution or a base of a cation infusate container. Handle 305 can be included to carry or move the infusate holder 301.

The bottom portions 302, 303, and 304 can act as fitting features on an exterior of the infusate holder 301. A complementary fitting feature on the interior surface of the receiving compartment of a dialysis machine can engage with the bottom portions 302, 303, and 304 to ensure the infusate holder 301 is properly positioned in the receiving compartment. For example, the interior surface of the receiving compartment can have indentations corresponding in position to the bottom portions 302, 303, and 304 that extend downwardly from the base of the infusate holder 301. The infusate holder 301 can only be placed in the receiving compartment in a configuration where the bottom portions 302, 303, and 304 are aligned with the indentations on the interior surface of the receiving compartment. The interior surface of the receiving compartment can have other fitting features, such as a protrusion, indentation, groove, or ridge positioned wherein the fitting feature has a shape, size, and/or geometry that is complementary to a corresponding fitting feature on an exterior surface of the infusate holder 301. Curves, wedges, indentations, or ridges can all be placed on an exterior surface of the infusate holder 301 and the interior surface of the receiving compartment to ensure the proper configuration of the infusate holder 301. The fitting feature is not limited to protrusions, indentations, grooves, or ridges, and can include various sizes and/or shapes of the receiving compartment or infusate holder 301. For example, a depth, incline, or diameter of the receiving compartment can serve as a fitting feature and the depth, incline, or diameter of the infusate holder 301 can serve as a complementary surface.

As illustrated in FIG. 3B, the infusate holder 301 can include a lid 306 with openings 307, 308, and 309 for connection of a dialysis fluid line or fluid connector to the infusate solutions or infusate containers. The openings 307, 308, and 309 are aligned with interior compartments 312, 313, and 314 illustrated in FIG. 3E. The lid 306, when placed on top of the infusate holder 301, can form an air tight seal with the infusate holder 301 and interior compartments. The air tight seal prevents air or fluids from contaminating the infusates when the infusate holder 301 is not used with separate infusate containers.

As illustrated in FIG. 3E, when used without separate infusate containers, the infusate holder 301 can include draw tubes to draw an infusate solution out of the bottom portions 302, 303, and 304 of the infusate holder 301. One or more upwardly extending interior walls 310 and 311 separate the infusate holder 301 into interior compartments 312, 313, and 314, each holding an infusate for addition to a dialysate flow path. For use with a solid or powdered infusate source, each interior compartment can include a filter, such as filter 317 in interior compartment 312 and filter 318 in interior compartment 313. The solid or powdered infusate source, such as solid sodium chloride, solid sodium bicarbonate, or a solid cation infusate source, can be placed above the filters 317 and 318. Water from the dialysis system can be added to the interior compartments 312 and 313 to dissolve all or a portion of the solid infusate source. The filters 317 and 318 prevent solids from moving into the bottom portions 302 and 303 of the interior compartments 312 and 313. Draw tubes 315 and 316 extend downwardly through the interior compartments 312 and 313, and through the filters 317 and 318. The infusate solutions in the bottom portions 302 and 303 can be pumped through the draw tubes 315 and 316 and into fluid lines (not shown in FIG. 3) fluidly connected to the draw tubes 315 and 316. As illustrated in FIGS. 3A and 3E, the exterior wall of the infusate holder 301 and upwardly extending interior walls 310 and 311 can include an inwardly tapered portion 319 in at least one interior compartment 313 for holding sodium bicarbonate. The inwardly tapered portion 319 greatly increases the efficiency of sodium bicarbonate delivery. Due to the solubility and particle size of solid sodium bicarbonate, the inwardly tapered portion 319 allows more efficient dissolving and delivery of the solid sodium bicarbonate, increasing efficiency to over 90% from about 50% efficiency without the tapered portion 319. Due to the greater solubility and smaller particle size of sodium chloride, the interior compartment 312 for holding sodium chloride does not require a tapered portion.

The tapered bottom portion of the sodium bicarbonate compartment can be included in any described embodiment of the infusate holder. A disposable or reusable sodium bicarbonate container can also include a tapered portion, and the infusate holder can be sized and shaped complementary to the inwardly tapered sodium bicarbonate container where separate containers are used.

Figure 7A:
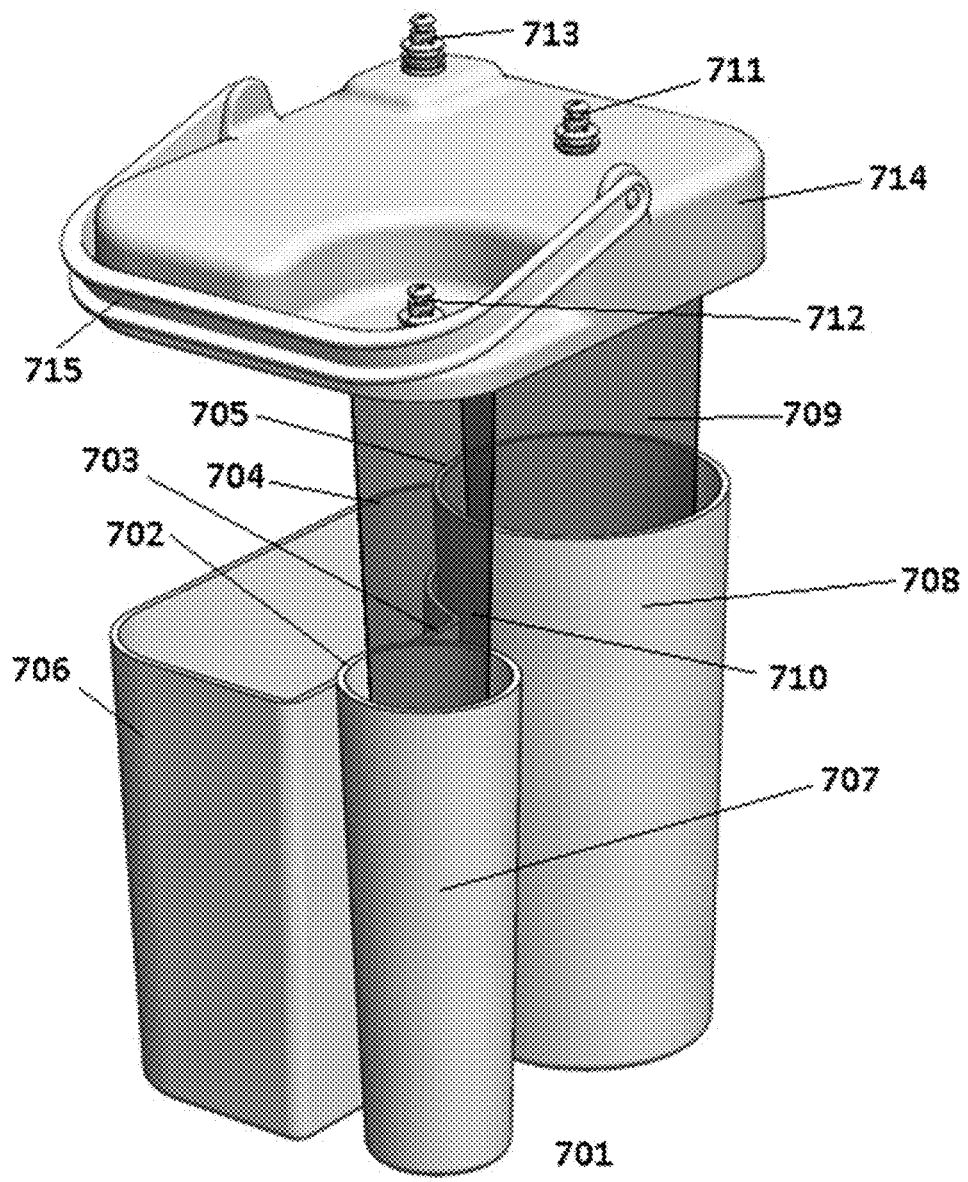
FIGS. 7A-C show an infusate holder for use with integrally formed disposable infusate containers.
Figure 7B:
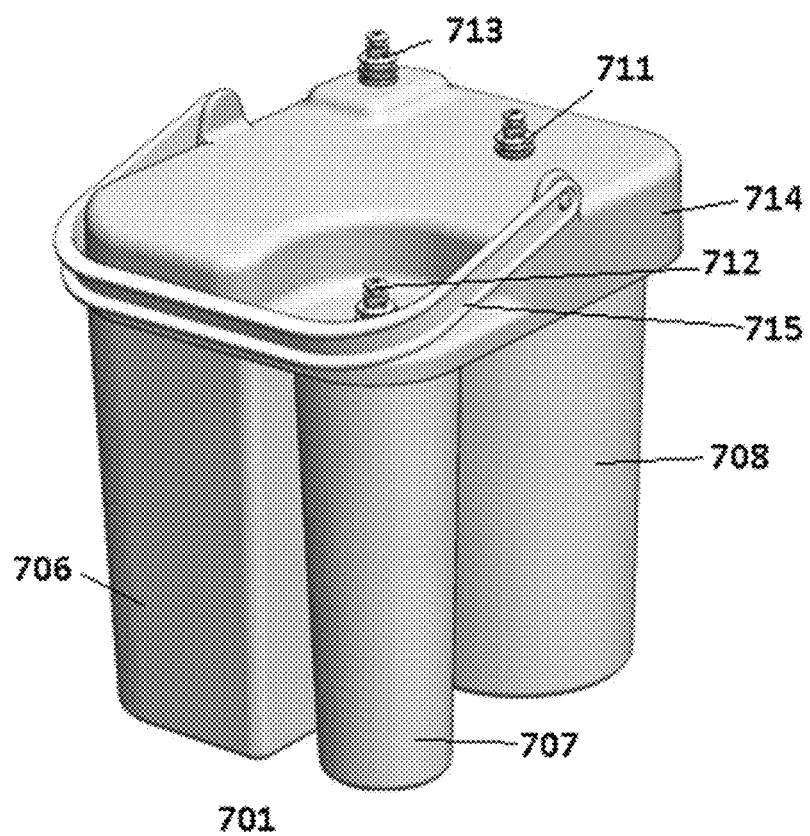
Figure 7C:
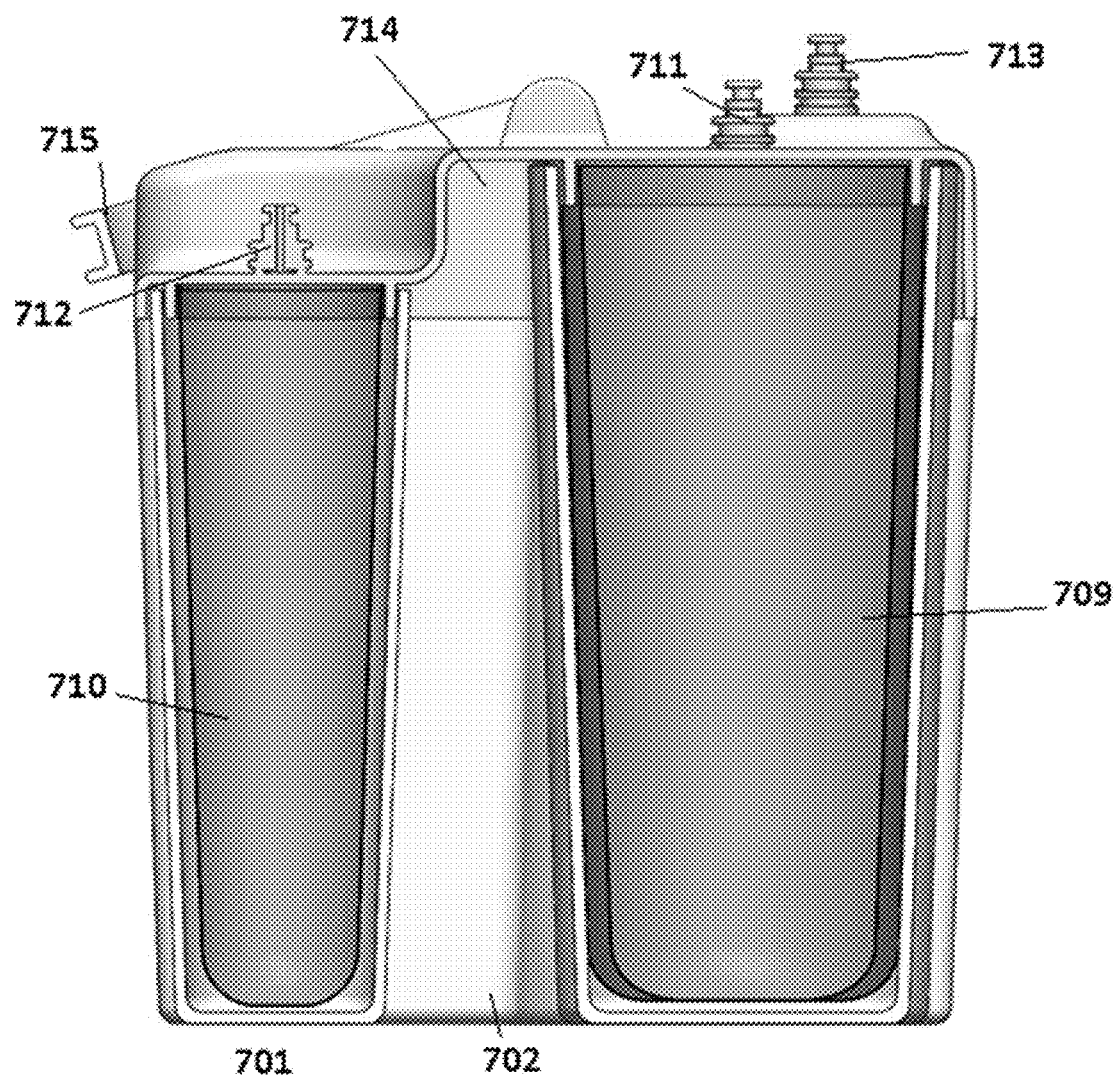

FIGS. 7A-C illustrate an infusate holder 701 with a disposable lid 714 integrally formed with disposable sodium bicarbonate container 709 and sodium chloride container 710. Additional disposable or reusable infusate containers (not shown) can be included in the infusate holder 701. FIG. 7A illustrates the infusate holder 701 with the lid 714 detached, FIG. 7B illustrates the infusate holder 701 after attaching the lid 714, and FIG. 7C is a cutaway view of the infusate holder 701 after attaching the lid 714. Upwardly extending interior walls 702, 703, 704, and 705 define interior compartment 708 for holding a sodium bicarbonate container 709, interior compartment 707 for holding a sodium chloride container 710, and interior compartment 706 for holding an additional infusate container (not shown). The sodium bicarbonate container 709 and sodium chloride container 710 can be integrally formed with the lid 714. When the lid 714 is placed on the infusate holder 701, as illustrated in FIG. 7B, the sodium bicarbonate container 709 and sodium chloride container 710 are placed within interior compartments 708 and 707 respectively. Fluid connector 711 provides for fluid ingress and egress from sodium bicarbonate container 709, and fluid connector 712 provides for fluid ingress and egress from sodium chloride container 710. Fluid connector 713 can connect to a disposable or non-disposable cation infusate container (not shown). Handle 715 can be included for easy maneuverability of the infusate holder 701.

To use the disposable sodium chloride container 710 and sodium bicarbonate container 709, fluid from a dialysate flow path (not shown) is added to solid infusate sources within the container. The addition of fluid from the dialysate flow path pressurizes the container. The interior and exterior walls of interior compartments 706, 707, and 708 provide support for the pressurized flexible infusate containers, preventing the containers from tearing during use, as illustrated in FIG. 7C. As described, the interior compartment 708 and disposable sodium bicarbonate container 709 can each have a tapered bottom portion (not shown in FIGS. 7A-C) to increase efficiency of sodium bicarbonate delivery.

Figure 8A:
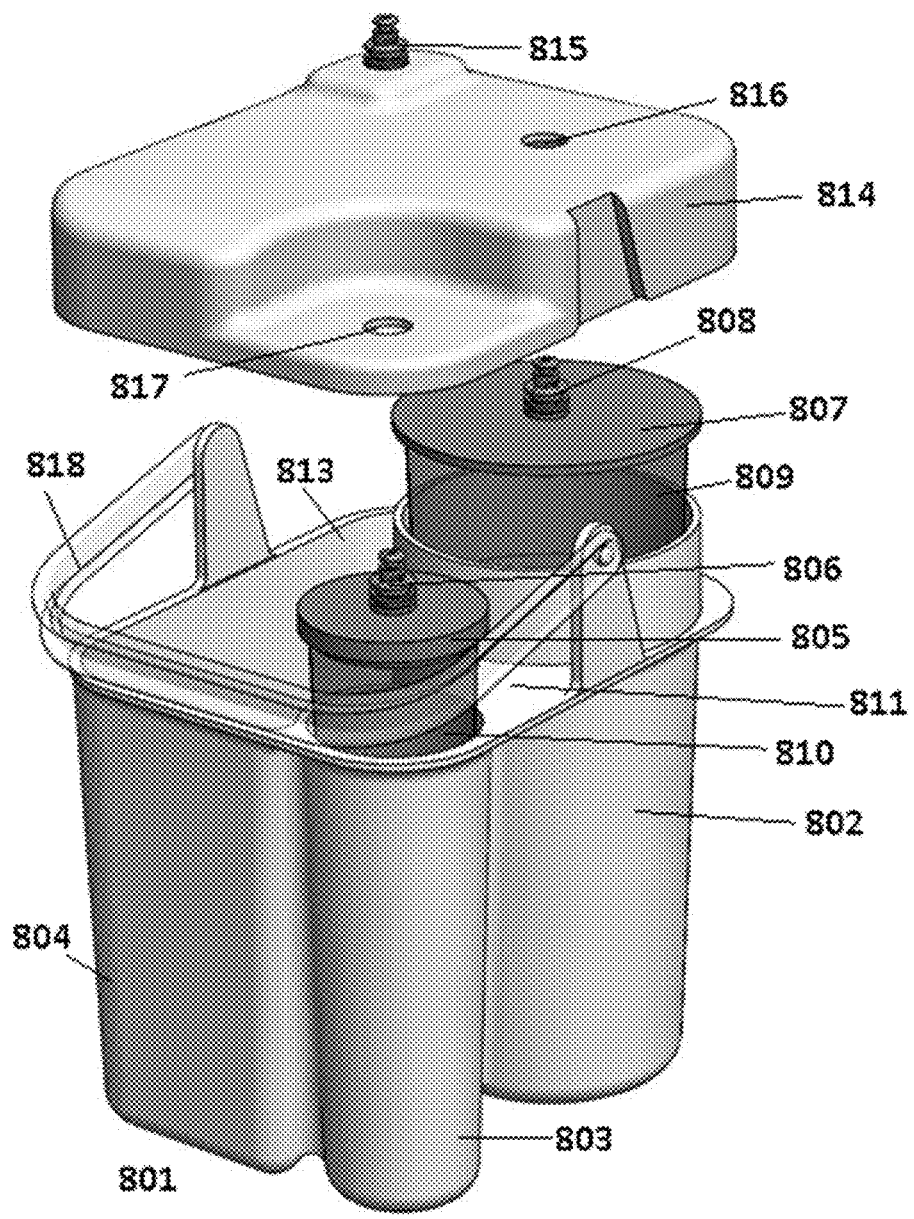
FIGS. 8A-B show an infusate holder for use with separate disposable infusate containers.
Figure 8B:
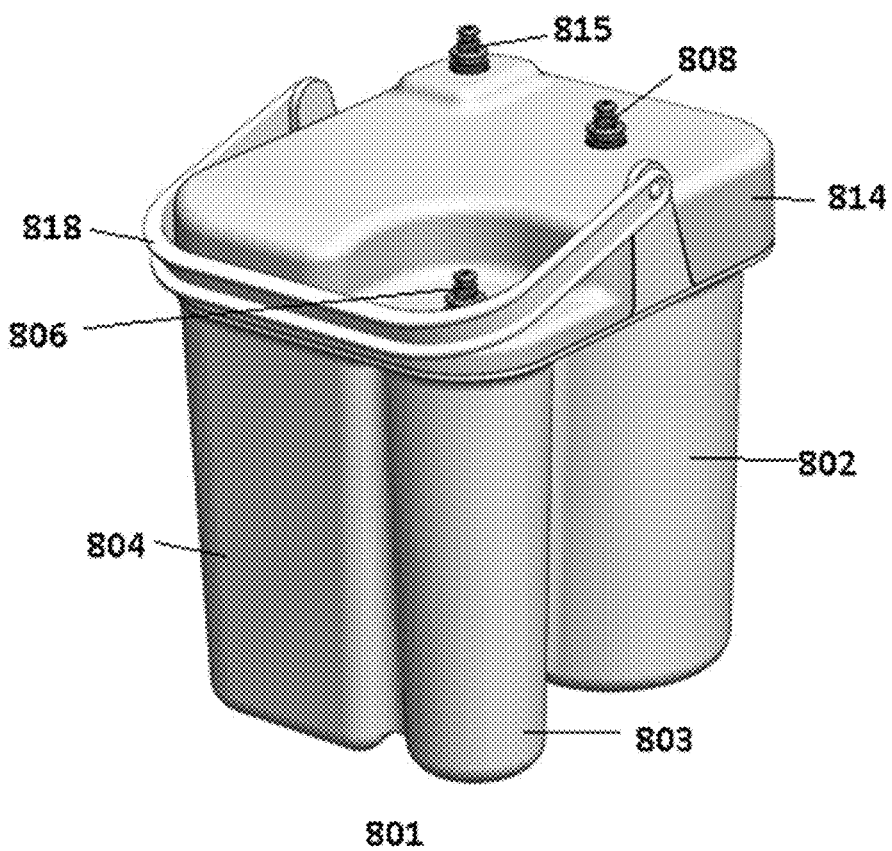

FIGS. 8A-B illustrate an infusate holder 801 with a reusable lid 814 formed separately from disposable sodium bicarbonate container 809 and sodium chloride container 810. FIG. 8A illustrates the infusate holder 801 with the lid 814 detached, and FIG. 8B illustrates the infusate holder 801 after attaching the lid 814. The disposable sodium bicarbonate container 809 and sodium chloride container 810 can be integrally formed with or attached to caps 807 and 805, respectively. The caps 807 and 805 can include connectors 808 and 806 for connection to a dialysis system. Exterior walls 802, 803 and 804, as well as interior wall 811 can form an interior compartment for the sodium bicarbonate container 809 and sodium chloride container 810, as well as one or more additional interior compartments 813 for additional infusate containers (not shown). The lid 814 can include opening 816 for insertion of connector 808 and opening 817 for connector 806. The openings 816 and 817 are aligned with the interior compartments for insertion of the connectors 808 and 806. An additional connector 815 can be included in the lid for connection to a cation infusate container or other container (not shown). Alternatively, the other container can include a connector, and a third opening can be included in the lid in place of connector 815. Handle 818 can be included for easy maneuverability of the infusate holder 801.

Figure 4:
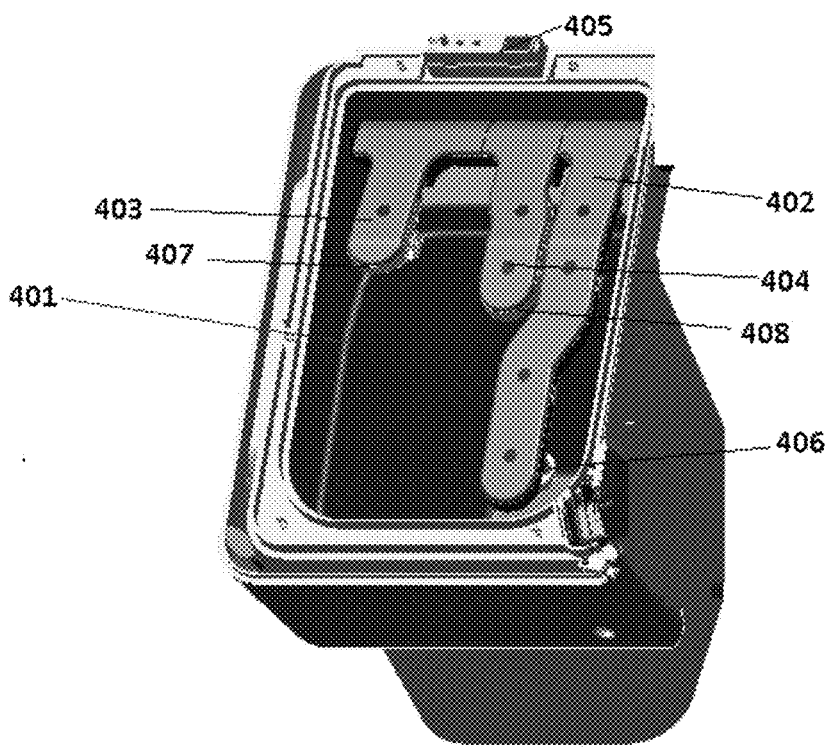
FIG. 4 is a receiving compartment of a dialysis machine.

FIG. 4 illustrates a receiving compartment 401 of a dialysis machine for receiving an infusate holder. The infusate holder can be placed in the receiving compartment 401. When the infusate holder is inserted into the receiving compartment 401, the interior compartments in the infusate holder will be structurally aligned with fluid connectors on the dialysis machine. For example, fluid connector 407 can be structurally aligned with the interior compartment for the sodium bicarbonate container, solid, or solution. Fluid connector 408 can be structurally aligned with the interior compartment for the sodium chloride container, solid, or solution. Fluid connector 406 can be structurally aligned with the interior compartment for the cation infusate container, solid, or solution.

The receiving compartment 401 can be sized and shaped complementary to the infusate holder. The receiving compartment 401 and infusate holder can be various shapes, including rectangular shaped, circular shaped, oval shaped, triangle shaped, square shaped, or other shapes. Further, the infusate holder and receiving compartment 401 can be shaped to ensure that the infusate holder is only inserted in the proper orientation to align the interior compartments with the proper fluid connectors. For example, the receiving compartment 401 can have a smaller size or shape at one end and a larger size or shape on a second end. The infusate holder can be sized and shaped complementary, with different sizes or shaped on different ends of the infusate holder. The infusate holder will only be insertable into the receiving compartment 401 in a single orientation where the complementary sizes and shapes of the receiving compartment 401 and infusate holder match.

In addition to sizing and shaping the interior compartments of the infusate holder to the infusate containers, an exterior surface of the fluid connectors can have a fitting feature to ensure proper mating to corresponding infusate container or draw tube. For example, a first fluid connector can have a hexagonal-shape while a second fluid connector can have a circular-shape. The corresponding infusate containers or draw tubes can have surfaces matched to receive the hexagonal- or circular shaped fluid connectors. The fluid connectors and container connectors or draw tubes can have a complementary shape, including circular, rectangular, square, triangular, hexagonal, or any other shape known in the art.

In FIG. 4, the fluid connectors 407, 408, and 406 are disposed on moveable paddles 403, 404, and 402, respectively. The paddles 403, 404, and 402 can be rotated about a hinge. The paddles 403, 404, and 402 can be moved upward to facilitate insertion of the infusate holder into the receiving compartment 401. After insertion, the paddles 403, 404, and 402 can be moved downward to place the fluid connectors 407, 408, and 406 in position to connect to each of the infusate containers or draw tubes. However, the fluid connectors 407, 408, and 406 need not be included on paddles, and can be included on a length of hose, wherein the hose is fluidly connected to a dialysate flow path. The hose can be selected from a range of materials known in the art for use in dialysis systems, including silicone, reinforced silicone, or PVC. One skilled in the art will understand that other biocompatible materials can be used for the hose, and the hose is not limited to any particular materials. The hoses can be either flexible or semi-rigid, which would allow the hoses to move for connection to the containers in the infusate holder. The hoses can be sized and positioned such that each hose will only be able to connect with a single container or draw tube within the infusate holder. For example, each hose may be positioned on a specific location with respect to the receiving compartment 401, and each hose can be short enough so that the hose cannot reach any interior compartment of the infusate holder not aligned with the specific location of the hose.

The receiving compartment 401 and infusate holder can also include an optional locking mechanism to keep the infusate holder from moving after insertion into the receiving compartment 401 when used with a removeable infusate holder. Non-limiting examples of locking mechanisms include latches that engage when the infusate holder is inserted in the receiving compartment 401. The infusate holder cannot be moved once the latches are engaged until a user disengages the latches. The locking mechanism can be positionable in an open state, which will allow removal of the infusate holder or a locked state, which will prevent the infusate holder from moving. A range of locking mechanisms known in the art can keep the infusate holder from moving within the receiving compartment 401.

Figure 5:
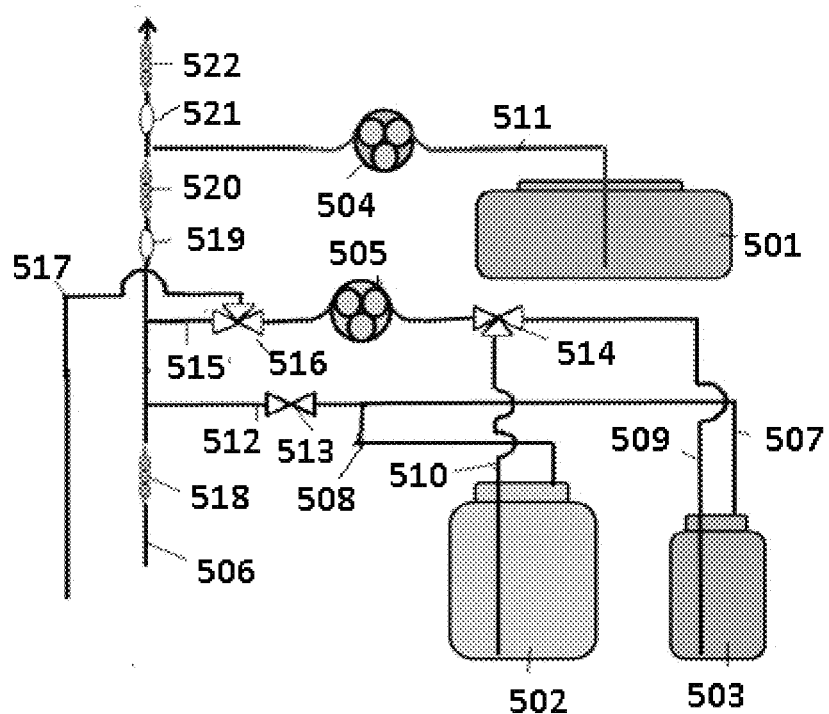
FIG. 5 is a flow diagram of the infusates in the infusate holder.

FIG. 5 illustrates a non-limiting flow diagram for infusates in an infusate holder fluidly connected to a dialysate flow path 506. Although shown as using separate infusate containers in FIG. 5, one of skill in the art will understand that the same flow diagram can be used with solid infusate sources or infusate solutions placed directly in the interior compartments of the infusate holder. The infusate holder can contain a cation infusate container 501, a sodium bicarbonate container 502, and a sodium chloride container 503, each of which can contain a solid source or a concentrate. Alternatively, the infusate holder can hold a solid or concentrate source of the infusates directly without any containers. Because the fluid connectors and fluid lines of the dialysis machine are structurally aligned to the interior compartments of the infusate holder, the infusates can only be fluid connected to the specific fluid connectors aligned with the interior compartments, ensuring that the proper chemicals are added to a dialysate flow path 506 at the proper locations. Additional containers or interior compartments can be included in the infusate holder as necessary.

Sodium chloride container 503 can be connected to fluid lines 507 and 509. Fluid line 507 can connect the sodium chloride container 503 to valve 513. Valve 513 can also connect to fluid line 512, which in turn connects to the main dialysate flow path 506 allowing fluid from the dialysate flow path 506 to enter the sodium chloride container 503. Fluid line 509 can connect to valve 514, which also connects to valve 516 downstream of pump 505. Pump 505 can control fluid flow through line 509 and valve 516, and can be a bidirectional pump. Valve 516 can be operated to direct fluid into the main dialysate flow path 506 during treatment by fluid line 515, or alternatively to direct fluid through fluid line 517 to a separate portion of the dialysate flow path 506. As described, directing sodium chloride and sodium bicarbonate upstream of a sorbent cartridge (not shown in FIG. 5) can reduce the time necessary for priming the dialysis machine. Valve 516 allows the sodium chloride and sodium bicarbonate to be pumped either upstream or downstream of the sorbent cartridge during priming and treatment, respectively.

Sodium bicarbonate container 502 can be connected to fluid lines 510 and 508. Fluid line 508 can also connect to valve 513 and can allow fluid from the dialysate flow path 506 to enter the sodium bicarbonate container 502. Fluid line 510 can also connect to valve 514. Cation infusate container 501 can be connected by fluid line 511 to the main dialysate flow path 506. Pump 504 can control fluid flow through line 511. Either or both of pumps 504 and 505 can be bi-directional pumps to move fluid from the containers within the infusate holder to the main dialysate flow path 506, or from the main dialysate flow path 506 to any of the containers within the infusate holder.

During treatment, various sensors can determine the concentration of sodium chloride, sodium bicarbonate, and cations added to the dialysate flow path 506 from the infusate holder containers. Conductivity sensor 518 can determine the conductivity of the dialysate prior to addition of sodium bicarbonate, sodium chloride, or other cations. Based on the conductivity detected by conductivity sensor 518, the amount of each fluid that needs to be added to the dialysate can be determined. Conductivity sensor 520, located downstream of fluid line 515, can determine the conductivity of the dialysate after addition of sodium bicarbonate, and ensures that the correct amount of sodium bicarbonate is added to the dialysate. Static mixer 519 can ensure complete mixing of the added sodium bicarbonate and the dialysate for accurate measurements by conductivity sensor 520. Conductivity sensor 522, located downstream of fluid line 511, can determine the conductivity of the dialysate after addition of the cation infusates, and ensure that the correct amount the cations is added to the dialysate. Conductivity sensor 522 can also provide a final check of the dialysate conductivity prior to the dialysate entering the dialyzer (not shown in FIG. 5). If the detected conductivity is outside of a predetermined range, the system can provide an alert, shutdown, or bypass the dialyzer to avoid delivering an unsafe dialysate to the patient. Static mixer 521 can ensure complete mixing of the added cation infusates and the dialysate for accurate measurements by conductivity sensor 522. One of skill in the art will understand that alternative arrangements of fluid lines, pumps, and valves are possible with the infusate holder of FIG. 5. The static mixers and sensors illustrated in FIG. 5 can be included in any described infusate holder configuration.

Figure 6:
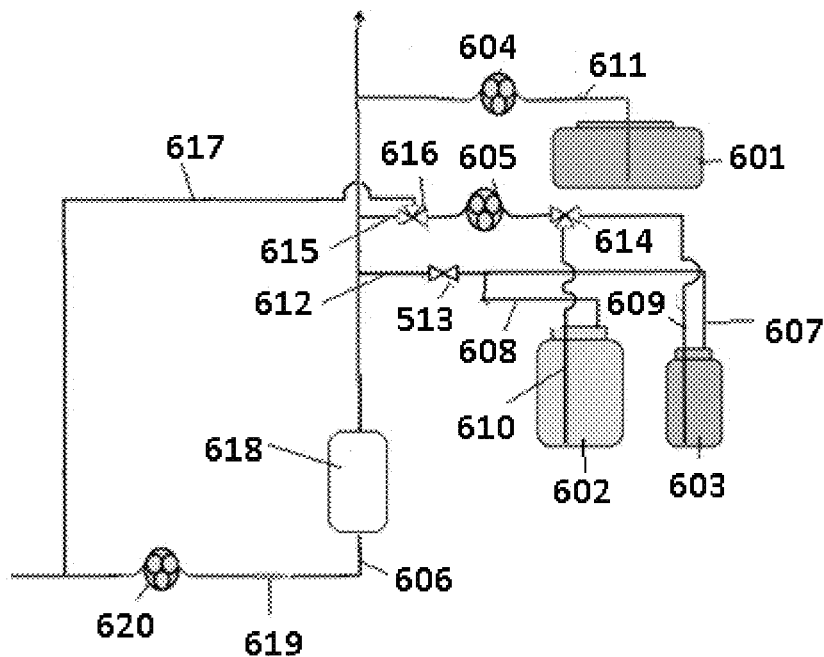
FIG. 6 is a dialysate flow path including the infusates in the infusate holder.

FIG. 6 illustrates a simplified portion of a dialysate flow path 606 using the infusate holder flow diagram. Sodium chloride container 603 can be connected to fluid lines 607 and 609. Fluid line 607 can connect the sodium chloride container 603 to valve 613. Valve 613 can also connect to fluid line 612, which in turn connects to the main dialysate flow path 606 allowing water from the dialysate flow path 606 to enter the sodium chloride container 603 for priming of the sodium chloride container 603. Fluid line 609 can connect to valve 614, which also connects to valve 616 downstream of pump 605. Pump 605 can control fluid flow through line 609 and valve 616. Valve 616 can be selectively openend and closed to direct fluid into the main dialysate flow path 606 during treatment by fluid line 615, or alternatively to direct fluid through fluid line 617 to a separate portion of the dialysate flow path 606.

Sodium bicarbonate container 602 can be connected to fluid lines 610 and 608. Fluid line 608 can also connect to valve 613 and can allow water from the dialysate flow path 606 to enter the sodium bicarbonate container 602. Fluid line 610 can also connect to valve 614. Cation infusate container 601 can be connected by fluid line 611 to the main dialysate flow path 606. Pump 604 can control fluid flow through line 611.

As described, valve 616 allows fluid to be directed to the dialysate flow path 606 upstream of sorbent cartridge 618. To reuse a dialyzer (not shown in FIG. 6), the dialyzer can be sterilized with a disinfectant solution. The disinfectant solution must then be flushed out of the dialyzer and dialysate flow path 606 by pumping fluid through the dialysate flow path 606. The sorbent cartridge 618 must then be flushed, drained, conditioned with sodium bicarbonate and primed with sodium chloride. Without valve 616, sorbent cartridge 618 can fill with water prior to conditioning. The sorbent cartridge 618 can then be flushed with additional sodium bicarbonate solution that has passed through the entire dialysate flow path 606 for conditioning. By directing the sodium bicarbonte through fluid line 617 upstream of the sorbent cartridge 618, only fluid with sodium bicarbonate enters the sorbent cartridge 618, reducing the time necessary for conditioning of the sorbent cartridge 618. After conditioning, the sorbent cartridge 618 is primed with a sodium chloride solution. By directing the sodium chloride through fluid line 617 upstream of the sorbent cartridge 618, only fluid with sodium sodium chloride enters the sorbent cartridge 618, reducing the time necessary for priming of the sorbent cartridge 618. The total time for conditioning and priming the system can be reduced by as much as 5-15 minutes by directing fluid upstream of the sorbent cartridge 618 with valve 616. Pump 620 provides the driving force for conveying dialysate and priming solution through the dialysate flow path 606. Conductivity sensor 619 detects the conductivity of the fluid prior to entering the sorbent cartridge 618. The conductivity of the fluid, along with the flow rate of the fluid, can be used determine an amount of bicarbonate and sodium chloride pumped through the dialysate flow path 606, allowing closed loop control during priming and flushing. One of skill in the art will understand a valve similar in function to valve 616 can be included in any of the described infusate holder configurations.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. An infusate holder, comprising:
   (i) a base;
   (ii) exterior walls connected to the base and upwardly extending from the base;
   (iii) at least two interior compartments; wherein the at least two interior compartments are each configured to receive and are complementary to one of at least two infusate containers; and
   (iv) wherein each of the at least two infusate containers holds at least one infusate selected from the group of a solution source, a solid infusate source, or a powdered infusate source;
   (v) the at least two interior compartments each having an interior wall connected to the base and upwardly extending from the base and defining each interior compartment of the infusate holder wherein a vertical axis of each interior compartment is aligned to one or more fluid connectors disposed on a dialysis machine; and
   (vi) wherein the infusate holder is complementary to a receiving compartment on the dialysis machine;
   wherein each of the at least two interior compartments are complementary to one of the at least two infusate containers;
   wherein every interior compartment included in the infusate holder has a size and/or shape different from every other interior compartment; the at least two interior compartments configured to define only one arrangement of the at least two infusate containers within the infusate holder;

the one or more fluid connectors fluidly connectable to the at least two infusate containers; and wherein the one or more fluid connectors disposed on the dialysis machine are positioned on one or more moveable paddles; the one or more moveable paddles rotatable around a hinge; wherein the one or more fluid connectors fluidly connect the at least two infusate containers to at least one fluid line on a fluid flow path.

2. The infusate holder of claim 1, wherein at least one of the at least two interior compartments contains a filter and a draw tube extending downwardly through the filter from a connector on top of the interior compartment.

3. The infusate holder of claim 1, further comprising a lid covering a top of the infusate holder, the lid having openings aligned with each of the interior compartments.

4. The infusate holder of claim 3, wherein the lid forms an air tight seal with each of the interior compartments.

5. The infusate holder of claim 1, at least one of the exterior walls and at least one of the interior walls defining at least one of the interior compartments having an inwardly tapered bottom portion.

6. The infusate holder of claim 1, wherein at least one of the at least two interior compartments comprises a fitting feature configured along the interior wall wherein the fitting feature is selected from the group of a protrusion, an indentation, a groove, a ridge, a curve, a wedge, and a complementary surface comprising a specified depth, incline, or diameter capable of forming a connection or fit to a corresponding fitting feature.

7. The infusate holder of claim 1, wherein the at least two interior compartments comprise at least four interior compartments; wherein each of the at least four interior compartments have a size and/or shape different from each of the other interior compartments.

8. A dialysis system, comprising:
an infusate holder; the infusate holder comprising:
(i) a base;
(ii) exterior walls connected to the base and upwardly extending from the base; and
(iii) at least two interior compartments; wherein each of the at least two interior compartments are each configured to hold one of at least two infusate containers; the at least two interior compartments each having an interior wall connected to the base and upwardly extending from the base and defining each interior compartment of the infusate holder wherein a vertical axis of each interior compartment is aligned to one or more fluid connectors disposed on a dialysis machine; and
(iv) wherein the infusate holder is complementary to a receiving compartment on the dialysis machine; and the dialysis machine, comprising:
(i) a dialysate flow path;
(ii) the receiving compartment on the dialysis machine having a size and shape complementary to the infusate holder;
(iii) the one or more fluid connectors fluidly connecting each of the infusate containers to the dialysate flow path; and
(iv) at least one pump controlling fluid movement through the one or more fluid connectors;

wherein each of the at least two interior compartments are complementary to one of the at least two infusate containers;

wherein every interior compartment included in the infusate holder has a size and/or shape different from every other interior compartment; the at least two interior compartments configured to define only one arrangement of the at least two infusate containers within the infusate holder;

the one or more fluid connectors fluidly connectable to each infusate container; and wherein the one or more fluid connectors disposed on the dialysis machine are positioned on one or more moveable paddles; the one or more moveable paddles rotatable around a hinge; wherein the one or more fluid connectors fluidly connect the at least two infusate containers to at least one fluid line on the dialysate flow path.

9. The dialysis system of claim 8, wherein the infusate containers are selected from the group consisting of a sodium bicarbonate container, a sodium chloride container, a cation infusate container, and combinations thereof.

10. The dialysis system of claim 8, further comprising a lid for the infusate holder, the lid having two or more openings aligned with the at least two interior compartments.

11. The dialysis system of claim 8, the infusate holder comprising at least a third interior compartment.

12. The dialysis system of claim 8, wherein the infusate containers contain infusates selected from the group consisting of sodium bicarbonate, sodium chloride, and cation infusates.

13. The dialysis system of claim 8, further comprising a lid for the infusate holder, the lid having two or more openings aligned with the at least two interior compartments.

14. The dialysis system of claim 13, the lid forming an air tight seal with the infusate holder.

15. The dialysis system of claim 13, further comprising draw tubes in each of the at least two interior compartments, the draw tubes extending downwardly from the openings in the lid into each of the at least two interior compartments; the draw tubes fluidly connectable to the one or more fluid connectors.

16. The dialysis system of claim 15, further comprising a filter within at least one of the at least two interior compartments, the filter disposed above the base of the infusate holder; at least one of the draw tubes extending through the filter.

17. The dialysis system of claim 8, further comprising a locking mechanism preventing the infusate holder from moving after insertion into the receiving compartment when the locking mechanism is in a locked state.

18. The dialysis system of claim 8, wherein the infusate holder is removable from the dialysis machine.

19. The dialysis system of claim 18, further comprising a handle disposed on at least one of the exterior walls of the infusate holder.

20. The dialysis system of claim 8, wherein at least one of the at least one pump is a bidirectional pump.

21. The dialysis system of claim 12, wherein the two or more infusate containers comprise an infusate container containing sodium chloride and an infusate container containing sodium bicarbonate; wherein the infusate container containing sodium chloride and the infusate container containing sodium bicarbonate are fluidly connectable to a valve; wherein the valve is fluidly connected to the dialysate flow path upstream of a sorbent cartridge and downstream of the sorbent cartridge.

22. The dialysis system of claim 8, further comprising at least one fitting feature on an exterior surface of the infusate holder; the at least one fitting feature complementary to a corresponding fitting feature on an interior surface of the receiving compartment.

\* \* \* \* \*